United States Patent [19]

Shim

[11] 4,278,816
[45] Jul. 14, 1981

[54] PROCESS FOR PREPARING PHENOLS AND THIOPHENOLS

[75] Inventor: Kyung-sup Shim, Irvington, N.Y.

[73] Assignee: Stauffer Chemical Company, Westport, Conn.

[21] Appl. No.: 827,919

[22] Filed: Aug. 26, 1977

[51] Int. Cl.³ .................. C07C 149/28; C07C 37/055
[52] U.S. Cl. ......................... 568/67; 568/62; 568/65; 568/630; 568/706; 568/713; 568/716; 568/780
[58] Field of Search ...................... 260/609 D, 621 F; 568/62, 706, 65, 713, 67, 630, 716, 780

[56] References Cited

U.S. PATENT DOCUMENTS 2,903,484  9/1959  Hardy et al. ............... 260/609 F

FOREIGN PATENT DOCUMENTS 45-5531    2/1970   Japan ................... 260/609 D
46-8293    3/1971   Japan ................... 260/609 D
913585    12/1962   United Kingdom ......... 260/609 D Primary Examiner—Donald G. Daus
Assistant Examiner—M. C. Eakin
Attorney, Agent, or Firm—William C. Gerstenzang

[57] ABSTRACT

Phenols and thiophenols are produced by reacting the corresponding diphenyl ether compound with hydrogen sulfide in contact with an absorptive catalyst, such as charcoal, activated carbon, calcined petroleum coke, etc. Temperatures in the range of from about 300° to about 900° C. are employed.

14 Claims, 1 Drawing Figure

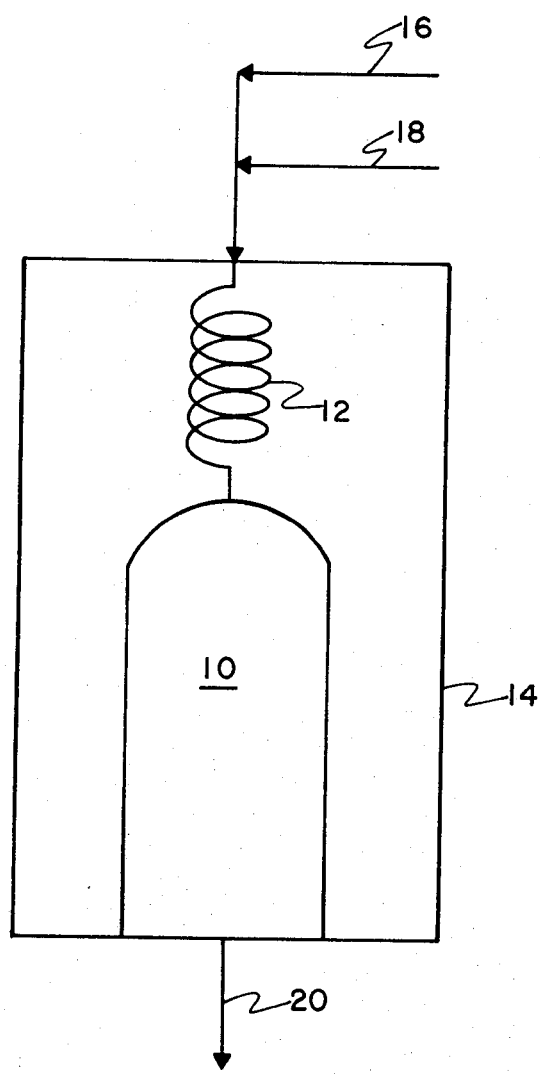
FIGURE

PROCESS FOR PREPARING PHENOLS AND THIOPHENOLS

BACKGROUND OF THE INVENTION

This invention relates to a process for the production of phenol and thiophenol compounds. Such compounds are well-known, phenols as solvents and intermediates and thiophenols as anti-oxidants, polymerization inhibitors, intermediates, etc.

Various processes for preparing thiophenols have previously been described. For example, U.S. Pat. No. 2,438,838 describes reacting a phenolic compound with hydrogen sulfide in the presence or absence of a dehydration catalyst at a superatmospheric pressure. Other methods are described in U.S. Pat. No. 2,490,257, directed to the vapor phase reaction of chlorobenzene and hydrogen sulfide in the presence of wood charcoal, and U.S. Pat. No. 3,799,989, directed to a non-catalytic process for preparing thiophenols from the same reactants.

Processes for preparing phenolic compounds have also been the subject of prior investigations. Thus, U.S. Pat. No. 2,862,035 discloses the treatment of ethers with an alkali metal and with molecular hydrogen to yield compounds containing hydroxyl groups and hydrocarbons, while German Patentschrift No. 730236 describes the cleavage of diphenylether in the presence of thorium oxide to provide phenol.

Methods involving the cleavage of certain diphenylethers to provide reaction products other than phenols have also been previously described. Thus, British Pat. No. 994,506 teaches the reaction of a phenol ether which contains at least one hydrogen atom in an ortho or para position to the —OH or ether group, with a sulfur chloride and hydrogen sulfide at a temperature in the range of from −50° C. to +200° C., recovering the polysulfide formed and reducing the polysulfide to the mercaptan.

However, all the prior art processes are subject to disadvantages in that they require costly catalytic or multi-step methods, or result in liberation of chlorine or hydrochloric acid, thus presenting pollution and environmental problems.

SUMMARY OF THE INVENTION

Now it has been found in accordance with this invention that phenols and thiophenols can be conveniently prepared from their corresponding diphenyl ether compounds in a one-step reaction which obviates the liberation of pollutants.

In the process of this invention, phenols and thiophenols are provided by reacting the corresponding diphenyl ether compounds with hydrogen sulfide in contact with an absorptive catalyst.

The invention will be better understood by reference to the following description and the accompanying drawing.

BRIEF DESCRIPTION OF THE DRAWING

The FIGURE is a diagrammatic representation of a process in accordance with this invention.

DETAILED DESCRIPTION OF THE INVENTION

More in detail, the phenols and thiophenols produced according to this invention include phenol and thiophenol, the latter also being known as phenyl mercaptan or phenyl thiol having the empirical formula $C_6H_5SH$, and substituted phenols and thiophenols. By the term "substituted phenols and thiophenols" in the claims and specification herein is meant phenols and thiophenols substituted on the benzene ring with one to five nitro, halogen, alkyl of 1 to 12 carbon atoms or alkoxy of from 1 to 6 carbon atoms, the substituents being identical or the same where more than one substituent is present.

As previously mentioned, one of the reactants in the method of this invention is the diphenyl ether compound corresponding to the desired phenol and thiophenol. Illustrative diphenyl ether compounds suitable for the practice of this invention include diphenyl ether, xylyl phenyl ether, o-chlorophenyl phenyl ether, p-fluorophenyl o-fluorophenyl ether, m-nitrophenyl phenyl ether, m-methylphenyl phenyl ether, p-dodecylphenyl phenyl ether, m-methoxyphenyl phenyl ether, o-hexyloxyphenyl phenyl ether, etc. The preferred diphenyl ether compound is the unsubstituted compound, diphenyl ether.

As an absorptive catalyst is used a material having a large surface area, in the order of about 1 to about 1000 square meters per gram. Suitable catalysts include active carbons, petroleum coke, various charcoals, calcined petroleum cokes, alumina, clay, silica gel, molecular sieve and various mixtures thereof. Optionally the absorptive catalysts can be admixed with, or impregnated with, co-catalysts such as zinc sulfide, cobalt sulfide, cadmium sulfide, and other transition metal sulfides and salts, and free transition metals such as molybdenum, cobalt, etc. Furthermore, various combinations of the aforementioned types of catalysts can be employed, such as mixtures of impregnated catalysts with non-impregnated catalysts, etc. The preferred catalysts are the charcoals and zinc sulfide-impregnated charcoals.

The reactants can be employed in stoichiometric amounts but preferably substantial excesses of hydrogen sulfide are used. Thus, it has been found that a 100% or greater excess of hydrogen sulfide is preferred.

While reaction temperatures from about 300° to about 900° C. can be suitably employed in the practice of this invention, preferably, the reaction is carried out at temperatures from about 450° to about 650° C. Pressure equipment can also be utilized and the reaction can be carried out at a pressure of up to 100 pounds per square inch absolute, and higher.

The reaction is carried out in the gaseous phase in any appropriate apparatus, such as static-bed reactors, fluid bed reactors, etc. Product can be recovered after one pass through the absorptive catalyst, or a continuous process wherein off-gas is recirculated can be provided. One method suitable for use in the practice of this invention is illustrated in the drawing.

Referring to the FIGURE, 10 represents a static-bed reactor containing an absorptive catalyst. Static-bed reactor 10 is connected to coiled preheating section 12 and both reactor 10 and preheating section 12 are positioned inside electric furnace 14. Hydrogen sulfide gas is fed in through line 16 and the diphenyl ether compound through line 18. The mixture of hydrogen sulfide gas and diphenyl ether compound is vaporized and preheated in section 12 at temperatures in the range of from about 300° to about 600° C., the specific temperatures being dependent upon the particular diphenyl ether compound employed. The gas mixture is then ssed through reactor 10 where temperatures of from out 300° to about 900° C. are maintained, and product ses leaving through line 20 are condensed to provide e desired phenol and thiophenol. Uncondensible by-oducts can be passed through a caustic scrubber (not own).

As previously mentioned, it is a feature of the process this invention that no corrosive and polluting by-products are formed. Thus, the unreacted hydrogen sulfide d diphenylether compound can be recycled without y by-product treatment to remove undesirable byoducts.

The mixture of phenols and thiophenols obtained in e process of this invention is conveniently separated conventional techniques such as distillation, solvent traction, etc. Both the phenols and thiophenols are eful products, obviating the need for by-product disosal.

The following examples will serve to illustrate the actice of this invention.

EXAMPLES 1-7

A static-bed reactor as illustrated in the FIGURE as employed in these examples. The reactor 10 consted of quartz glass 1 inch in diameter and 13 inches ng and was attached to a coiled preheating section 12, nsisting of ¼ inch diameter quartz tubing, 36 inches ng.

The reactor 10 was filled with coal charcoal and ated to the desired temperature; the preheater temrature was set at 400° C. Diphenylether was fed into e preheater at a rate of addition of 0.07 moles per urs and hydrogen sulfide was fed at a rate of 0.35 oles per hour. The reactants were vaporized and ated in the preheater prior to entering the reactor 10. e residence time in reactor 10 was 12 seconds.

The gaseous products were quenched in a water oled condenser and the products identified by comring gas-liquid chromatography retention times with ose of authentic samples of thiophenol and phenol. e reactor temperatures and the composition of the oducts are set forth in the table below; "tr" indicates at trace amounts of the specified materials was found.

| AMPLE | 1 | 2 | 3 | 4 | 5 | 6 | 7 |
|---|---|---|---|---|---|---|---|
| actor mperature °C. | 400 | 450 | 500 | 500 | 550 | 580 | 600 |
| duct mposition Wt % |  |  |  |  |  |  |  |
| enol and iophenol (50:50) | 13.1 | 26.3 | 25.2 | 28.8 | 18.8 | 19.7 | 21.2 |
| reacted henyl ether | 86.9 | 69.7 | 70.4 | 65.5 | 75.8 | 75.2 | 73.0 |
| nyl sulfide | tr | 2.2 | 3.6 | 5.7 | 4.7 | 5.1 | 5.8 |
| nyldisulfides | tr | 1.9 | 1 | tr | 1 | tr | tr |

EXAMPLES 8-13

In these examples, the equipment and procedure of amples 1-7 were employed, but zinc sulfide-impregted activated carbon was used as the absorptive matel instead of coal charcoal. The impregnated activated rbon was made according to conventional techniques wetting BPL activated carbon from PPG Industries, . with zinc acetate, drying the wet carbon and subseently passing H₂S through the dried material at 400° to convert the zinc acetate to zinc sulfide. The reacn temperatures and product compositions are set forth in the table below; "tr" indicates that trace amounts were found.

| EXAMPLES | 8 | 9 | 10 | 11 | 12 | 13 |
|---|---|---|---|---|---|---|
| Reactor Temperature °C. | 400 | 450 | 500 | 500 | 550 | 600 |
| Product Composition Wt % |  |  |  |  |  |  |
| Phenol and Thiophenol (50:50) | 35.4 | 31.8 | 35.7 | 26.1 | 26.1 | 29.8 |
| Unreacted Diphenyl ether | 63.2 | 62.2 | 52.8 | 69.2 | 68.9 | 63.6 |
| Phenyl sulfide | tr | 1.9 | 3.2 | 1.2 | 1.6 | 1.8 |
| Phenyldisulfides | tr | 4.1 | 3.6 | 1.9 | 1.2 | tr |

EXAMPLES 14-18

In these examples, the absorptive material was Girdler G35, an alumina support containing cobalt and molybdenum available from Girdler Chemical, Inc., P.O. Box 337, Louisville, Ky 40201. The reaction temperature and results are set forth in the table.

| EXAMPLES | 14 | 15 | 16 | 17 | 18 |
|---|---|---|---|---|---|
| Reactor Temperature °C. | 400 | 450 | 500 | 550 | 600 |
| Product Composition Wt % |  |  |  |  |  |
| Phenol and Thiophenol (50:50) | 18.4 | 22.6 | 25.7 | 20.0 | 15.8 |
| Unreacted Diphenyl ether | 57.7 | 52.6 | 57.1 | 54.1 | 50.7 |
| Phenyl sulfide | 2.9 | 5.1 | 5.2 | 3.2 | 6.7 |
| Phenyldisulfides | 10.8 | 10.9 | 11.7 | 13.0 | 10.4 |

What is claimed is:

1. A process for producing a phenol and a thiophenol which comprises reacting the corresponding diphenylether compound with hydrogen sulfide in the gaseous phase in contact with a catalyst comprising an absorptive catalyst.

2. The process of claim 1 wherein said reaction is carried out at a temperature of from about 300° to about 900° C.

3. The process of claim 2 wherein said reaction is carried out at a temperature of from about 450° to about 650° C.

4. The process of claim 1 wherein said absorptive catalyst has a surface area of about 1 to about 1000 square meters per gram.

5. The process of claim 4 wherein said absorptive catalyst is charcoal.

6. The process of claim 4 wherein at least part of said catalyst contains a co-catalyst.

7. The process of claim 6 wherein said co-catalyst is a transition metal sulfide.

8. The process of claim 7 wherein said catalyst is zinc sulfide-impregnated charcoal.

9. The process of claim 6 wherein said catalyst is silica containing colbalt and molybdenum.

10. The process of claim 1 wherein phenol and thiophenol are provided by reacting diphenylether with hydrogen sulfide.

11. The process of claim 10 wherein said reaction is carried out at a temperature of from about 300° to about 900° C.

12. The process of claim 11 wherein said absorptive catalyst is charcoal.

13. The process of claim 11 wherein said catalyst is silica containing cobalt and molybdenum.

14. The process of claim 11 wherein said catalyst is zinc sulfide-impregnated charcoal.

* * * * *